(12) United States Patent
Nelson et al.

(10) Patent No.: US 8,901,516 B2
(45) Date of Patent: Dec. 2, 2014

(54) EXCITATION LIGHT SOURCE ASSEMBLY

(75) Inventors: Michael B. Nelson, Tucson, AZ (US); Michael D. Cable, Tucson, AZ (US)

(73) Assignee: Spectral Instruments Imaging, LLC, Tuscon, AZ (US)

( * ) Notice: Subject to any disclaimer, the term of this patent is extended or adjusted under 35 U.S.C. 154(b) by 84 days.

(21) Appl. No.: 13/222,688

(22) Filed: Aug. 31, 2011

(65) Prior Publication Data

US 2012/0049089 A1     Mar. 1, 2012

Related U.S. Application Data

(60) Provisional application No. 61/379,282, filed on Sep. 1, 2010.

(51) Int. Cl.
*G01N 21/64* (2006.01)
*G03B 15/05* (2006.01)

(52) U.S. Cl.
CPC .......... *G01N 21/645* (2013.01); *G01N 21/6456* (2013.01); *G03B 15/05* (2013.01); *G01N 2021/6419* (2013.01); *G01N 2021/6421* (2013.01); *G01N 2021/6423* (2013.01); *G01N 2021/6471* (2013.01)
USPC .................................................. 250/461.1

(58) Field of Classification Search
CPC ............ G01N 21/645; G01N 21/6428; G01N 2021/7786; G01N 21/6458; G01N 2021/6463
USPC ....................................................... 250/461.1
See application file for complete search history.

(56) References Cited

U.S. PATENT DOCUMENTS

| | | | |
|---|---|---|---|
| 3,800,079 A | 3/1974 | McNeil et al. | |
| 3,871,767 A | 3/1975 | Holm-Hansen et al. | |
| 3,949,162 A | 4/1976 | Malueg | |
| 4,196,994 A | 4/1980 | de Jesus et al. | |
| 4,298,887 A | 11/1981 | Rode | |
| 4,343,021 A | 8/1982 | Frame | |

(Continued)

FOREIGN PATENT DOCUMENTS

| | | |
|---|---|---|
| EP | 0097060 A2 | 12/1983 |
| EP | 0228877 A2 | 7/1987 |

(Continued)

OTHER PUBLICATIONS

Haworth, "CCD Image Calibration Using AIP4WIN," http://www.stargazing.net/david, Copyright 2001 David Haworth v. 5.0, pp. 1-12.

(Continued)

*Primary Examiner* — Marcus Taningco
(74) *Attorney, Agent, or Firm* — Fennemore Craig, P.C.

(57) ABSTRACT

An excitation light source assembly includes a housing defining a central opening therein and a plurality of lamp receptacles surrounding the central opening. The housing is mountable to a support structure having a camera mounted thereto so that a field of view of the camera is substantially unobstructed by the housing. A light source is positioned within each of the plurality of lamp receptacles. A diffuser is positioned adjacent the light source in each of the plurality of lamp receptacles so that each of the diffusers diffuses light produced by each of the light sources. A control system operatively connected to each of the light sources operates selected ones of the light sources to provide a desired excitation illumination to an object within the field of view of the camera.

27 Claims, 12 Drawing Sheets

(56) References Cited

U.S. PATENT DOCUMENTS

| | | |
|---|---|---|
| 4,585,934 A | 4/1986 | French et al. |
| 4,593,728 A | 6/1986 | Whitehead et al. |
| 4,687,325 A | 8/1987 | Corby, Jr. |
| 4,863,690 A | 9/1989 | Berthold et al. |
| 4,885,544 A | 12/1989 | Tago |
| 4,948,975 A | 8/1990 | Erwin et al. |
| 5,008,548 A | 4/1991 | Gat |
| 5,039,868 A | 8/1991 | Kobayashi et al. |
| 5,089,895 A | 2/1992 | Fraker et al. |
| 5,202,091 A | 4/1993 | Lisenbee |
| 5,401,465 A | 3/1995 | Smethers et al. |
| 5,414,258 A | 5/1995 | Liang |
| 5,515,161 A | 5/1996 | Blumenfeld |
| 5,542,012 A | 7/1996 | Fernandes et al. |
| 5,587,583 A | 12/1996 | Chin et al. |
| 5,672,881 A | 9/1997 | Striepeke et al. |
| 5,680,492 A | 10/1997 | Hopler et al. |
| 5,689,110 A | 11/1997 | Dietz et al. |
| 5,818,977 A | 10/1998 | Tansley |
| 5,840,572 A | 11/1998 | Copeland et al. |
| 5,865,754 A | 2/1999 | Sevick-Muraca et al. |
| 5,898,802 A | 4/1999 | Chen et al. |
| 5,964,220 A | 10/1999 | Boussignac et al. |
| 5,984,494 A * | 11/1999 | Chapman et al. ............ 362/470 |
| 5,986,271 A | 11/1999 | Lazarev et al. |
| 6,004,767 A | 12/1999 | Crouch et al. |
| 6,033,087 A * | 3/2000 | Shozo et al. ................. 362/244 |
| 6,038,038 A | 3/2000 | Selby et al. |
| 6,097,025 A | 8/2000 | Modlin et al. |
| 6,154,277 A | 11/2000 | Snelling et al. |
| 6,205,244 B1 | 3/2001 | Bawolek et al. |
| 6,217,847 B1 | 4/2001 | Contag et al. |
| 6,377,353 B1 | 4/2002 | Ellis |
| 6,454,437 B1 | 9/2002 | Kelly |
| 6,614,452 B1 | 9/2003 | Cable |
| 6,642,499 B1 | 11/2003 | Boni et al. |
| 6,754,008 B1 | 6/2004 | Wallerstein et al. |
| 6,775,567 B2 | 8/2004 | Cable et al. |
| 6,894,289 B2 | 5/2005 | Nilson et al. |
| 6,901,279 B2 | 5/2005 | Cable et al. |
| 6,919,919 B2 | 7/2005 | Nelson et al. |
| 6,922,246 B2 | 7/2005 | Nilson et al. |
| 7,113,217 B2 | 9/2006 | Nilson et al. |
| 7,116,354 B2 | 10/2006 | Rice et al. |
| 7,177,024 B2 | 2/2007 | Nilson et al. |
| 7,190,991 B2 | 3/2007 | Cable et al. |
| 7,196,190 B2 | 3/2007 | Ning et al. |
| 7,255,851 B2 | 8/2007 | Contag et al. |
| 7,298,415 B2 | 11/2007 | Nilson et al. |
| 7,299,420 B2 | 11/2007 | Cable |
| 7,331,341 B2 | 2/2008 | Nelson |
| 7,383,078 B2 | 6/2008 | Cable et al. |
| 7,403,812 B2 | 7/2008 | Rice et al. |
| 7,449,567 B2 | 11/2008 | Zhang et al. |
| 7,449,615 B2 | 11/2008 | Contag et al. |
| 7,461,652 B2 | 12/2008 | Dalgetty et al. |
| 7,464,707 B2 | 12/2008 | Dalgetty et al. |
| 7,466,418 B2 | 12/2008 | Nilson et al. |
| 7,474,398 B2 | 1/2009 | Nilson et al. |
| 7,474,399 B2 | 1/2009 | Nilson et al. |
| 7,503,323 B2 | 3/2009 | Dalgetty et al. |
| 7,555,332 B2 | 6/2009 | Rice et al. |
| 7,555,334 B2 | 6/2009 | Coquoz et al. |
| 7,581,191 B2 | 8/2009 | Rice et al. |
| 7,589,786 B2 | 9/2009 | Nilson et al. |
| 7,595,838 B2 | 9/2009 | Nilson et al. |
| 7,599,731 B2 | 10/2009 | Rice et al. |
| 7,603,167 B2 | 10/2009 | Stearns et al. |
| 7,616,985 B2 | 11/2009 | Stearns et al. |
| 7,663,664 B2 | 2/2010 | Rice et al. |
| 7,690,801 B2 * | 4/2010 | Amphlett .......................... 362/3 |
| 2001/0028510 A1 | 10/2001 | Ramm et al. |
| 2004/0121175 A1 | 6/2004 | Flexman et al. |
| 2004/0247170 A1 | 12/2004 | Furze et al. |
| 2005/0265024 A1 | 12/2005 | Luk |
| 2009/0268426 A1 | 10/2009 | Pohlert et al. |
| 2011/0284765 A1 * | 11/2011 | Pieper et al. ............... 250/458.1 |

FOREIGN PATENT DOCUMENTS

| | | |
|---|---|---|
| EP | 0491131 A1 | 6/1992 |
| EP | 0493707 A2 | 7/1992 |
| EP | 0718622 A2 | 6/1996 |
| EP | 1478423 B1 | 7/2006 |
| EP | 1478916 B1 | 7/2008 |
| JP | 1040330 A | 2/1998 |
| WO | 9400742 A1 | 1/1994 |
| WO | 9908233 A1 | 2/1999 |
| WO | 0049938 A1 | 8/2000 |
| WO | 0161324 A1 | 8/2001 |
| WO | 0163247 A2 | 8/2001 |

OTHER PUBLICATIONS

Roda et al., "Chemiluminescence Imaging Systems for the Analysis of Macrosamples: Microtiter Format, Blot Membrane, and Whole Organs," Methods in Enzymology, vol. 305, Copyright 2000 by Academic Press, pp. 120-132.

Stanley, "Commercially Available Luminometers and Low-Level Light Imaging Devices," Methods in Enzymology, vol. 305, Copyright 2000 by Academic Press, pp. 96-103.

Ross et al., "High-speed radiometric imaging with a gated, intensified, digitally-controlled camera[2869-29]," http://ucla.worldcat.org, Proceedings—SPIE the International Society for Optical Engineering, No. 2869, (1996): 386-394, British Library Serials, 2 pages.

Rice et al., "In vivo imaging of light-emitting probes," Journal of Biomedical Optics, vol. 6, No. 4, Oct. 2001, pp. 432-440.

Hengerer et al., "In vivo Procedure for the Measurement Luciferase Reporter Gene Activity with a Low Light Imaging System," Reprint from BIOspektrum 4 (1998), pp. 1-3.

Berthold et al., "Luminometer Design and Low Light Detection," Methods in Enzymology, vol. 305, Copyright 2000 by Academic Press, pp. 62-87.

Brauer et al., "Measuring luminescence with a low light level imaging system using electronic light standards," Siemens AG, Karlsruhe, Germany, Bioluminescence & Chemiluminescence status report, Chichester:Wiley 1993: 13-17, 1 page.

Szalay et al., "Bioluminescence and chemiluminescence: status report: proceedings of the VIIth Bioluminescence and Chemiluminescence," Banff, Mar. 1993, http://ucla.worldcat.org, 1 page.

Francis et al.,"Monitoring Bioluminescent Staphylococcus aureus Infections in Living Mice Using a Novel luxABCDE Construct," http://iai.asm.org/cgi/content/full/68/6/3594, Xenogen Corporation, Alameda, CA and Division of Neonatal andDevelopmental Medicine, Department of Pediatrics, Stanford University Medical Center, Stanford, CA, Infection and Immunity, vol. 68, No. 6, Jun. 2000, cover page and pp. 3594-3600.

Voss et al., "Radiometric and Geometric Calibration of a Visible Spectral Electro-Optic 'Fisheye' Camera Radiance Distribution System," Journal of Atmospheric and Oceanic Technology, vol. 6, (1989), pp. 652-662.

Niles et al., "Radiometric calibration of a video fluorescence microscope for the quantitative imaging of resonance energy transfer," Rev. Sci, Instrum. 66 (6), Jun. 1995, Copyright 1995 American Institute of Physics, pp. 3527-3536.

Edirisinghe et al., "Radiometric Callibration of Multispectral Airborne Video Systems," International Journal of Remote Sensing, vol. 20, No. 14, 1999, cover page and pp. 2855-2870.

Rehemtulla et al.,"Rapid and Quantitative Assessment of Cancer Treatment Response Using In Vivo Bioluminescence Imaging," Neoplasia, vol. 2, No. 6, 2000, www.nature.com/neo, pp. 491-495.

Zhang et al., "Rapid in vivo funtional analysis of transgenes in mice using whole body imaging of luciferase expression," Transgenic Research 10: 2001 Kluwer Academic Publishers, The Netherlands, pp. 423-434.

(56) References Cited

OTHER PUBLICATIONS

Tsin et al., "Statistical Calibration of CCD Imaging Process," Appeared in the Proceedings of the IEEE 2001 International Conference on Computer Vision, pp. 1-8.

Contag et al., "Use of Reporter Genes for Optical Measurements of Neoplastic Disease In Vivo," Neoplasia, vol. 2, Nos. 1-2, Jan.-Apr. 2000, www.nature.com/neo, pp. 41-52.

Contag et al., "Visualizing Gene Expression in Living Mammals Using a Bioluminescent Reporter," Photochemistry and Photobiology, 1997, 66(4): pp. 523-531.

International Search Report and Written Opinion for PCT/US2011/049998, dated Dec. 22, 2011, 10 pages.

O'Kane et al., "Absolute Calibration of Luminometers with Low-Level Light Standards," Methods in Enzymology, vol. 305, Copyright 2000 by Academic Press, pp. 87-96.

Brown et al., "Absolute Radiometric Calibration of Digital Imaging Systems," IS&T/SPIE Electronic Imaging, San Jose, California, Jan. 2001, 9 pages.

Chen et al., "Auaomated Calibration of a Zoom Lens CCD Image System for Videogrammetry," International Archives of Photogrammetry and Remote Sensing, vol. XXXIII, Part B4, Amsterdam, The Netherlands, 2000, pp. 180-185.

Campbell et al., "Bioluminescence and Chemiluminescence," Proceedings of the 8th International Symposium of Bioluminescence and Chemiluminescence, Cambridge, Sep. 1994, John Wiley & Sons, 5 pages.

Contag et al., "Bioluminescent indicators in living mammals," Nature Medicine, vol. 4, No. 2, Feb. 1998, http://www.nature.com/naturemedicine, pp. 245-247.

Ochs et al., "Camera Types for Low Level Light Imaging," Oct. 1995, pp. 1-6.

Gatan, Inc., "CCD Image Acquisition Tutorial," Gatan, Inc., Pleasanton, California, May 2001, cover page and pp. 1-7.

\* cited by examiner

EXCITATION LIGHT SOURCE ASSEMBLY

CROSS-REFERENCE TO RELATED APPLICATION

This application claims the benefit of U.S. Provisional Patent Application No. 61/379,282, filed on Sep. 1, 2010, which is hereby incorporated herein by reference for all that it discloses.

TECHNICAL FIELD

This invention relates in general to systems for exciting fluorescent materials and more particularly to systems for exciting fluorescent materials in molecular imaging applications.

BACKGROUND

Molecular imaging systems are known in the art and are commonly used to capture various types or modes of images from an object or specimen being analyzed. The objects or specimens that are imaged may comprise any of a wide range of compositions and objects, as is well-known. Primarily, such imaging systems are configured to detect extremely low levels of light emitted by the specimen or object under study. The light emitted by the object or specimen may be generated by a bio-luminescence process, a fluorescence process, or by a combination thereof. Such imaging systems may also be capable of capturing reflected light images, in which light reflected by the object is captured by the imaging system camera. Such a reflected light image is often combined with one or more emitted light images to form a single, composite image. Such a composite image allows a user to more easily correlate features and attributes of the emitted light image(s) with physical locations on the specimen or other characteristics that are contained in the reflected light image.

As is known, light emission by fluorescence results from the prior or simultaneous exposure of the fluorescent material to excitation light of suitable wavelength. However, not all fluorescent materials fluoresce or emit light in response to excitation light of the same wavelength. Consequently, the wavelength of the particular excitation light must be selected so that it will excite the particular fluorescent material involved.

Because most molecular imaging systems seek to detect fluorescence from a wide range of fluorescent materials, most such imaging systems are provided with excitation light sources that can be operated to illuminate the fluorescent material with excitation light of the appropriate wavelength. Unfortunately, however, most excitation light sources tend to be expensive and/or difficult to implement in use, and systems are constantly being sought that improve on existing systems.

SUMMARY OF THE INVENTION

An excitation light source assembly according to one embodiment of the invention may include a housing defining a central opening therein and a plurality of lamp receptacles surrounding the central opening. The housing is mountable to a support structure having a camera mounted thereto so that a field of view of the camera is substantially unobstructed by the housing. A light source is positioned within each of the plurality of lamp receptacles. A diffuser is positioned adjacent the light source in each of the plurality of lamp receptacles so that each of the diffusers diffuses light produced by each of the light sources. A control system operatively connected to each of the light sources operates selected ones of the light sources to provide a desired excitation illumination to an object within the field of view of the camera.

Also disclosed is an excitation light source assembly that includes a housing and a first connector portion mounted to the housing. A lamp receptacle produces light in a first defined wavelength band. A second connector portion is mounted to the lamp receptacle so that the lamp receptacle can be removably engaged with the first connector portion mounted to the housing. The housing is mountable to a support structure so that a field of view of a camera also mounted to support structure is substantially unobstructed by the housing and by the lamp receptacle.

Another excitation light source assembly includes a base member that defines a central opening therein. A plurality of first connector portions are mounted to the base member at positions located around the central opening. The light source assembly also includes a plurality of lamp receptacles, at least some of which produce light in different wavelength bands. A second connector portion mounted to each of the plurality of lamp receptacles is releasably engagable with a corresponding one of the plurality of first connector portions mounted to the base member. The base member is mountable to a support structure so that the central opening is aligned with a camera mounted to the support structure and so that a field of view of the camera is substantially unobstructed by the base member and the lamp receptacles.

Also disclosed is an assembly that includes a support structure and a camera mounted to the support structure. An excitation light source assembly mounted to the support structure includes a housing that defines a central opening therein and a plurality of lamp receptacles that surround the central opening. The housing is mounted to the support structure so that the central opening is aligned with the camera and so that a field of view of the camera is substantially unobstructed by the housing. At least one narrow-band light source is positioned within at least one of the plurality of lamp receptacles. A diffuser is positioned adjacent the narrow-band light source. A control system operatively connected to each of the narrow-band light sources operates selected ones of the narrow-band light sources to provide a desired excitation illumination to a fluorescent material within the field of view of said camera.

BRIEF DESCRIPTION OF THE DRAWINGS

Illustrative and presently preferred exemplary embodiments of the invention are shown in the drawings in which.

DETAILED DESCRIPTION OF THE PREFERRED EMBODIMENTS

Figure 1:
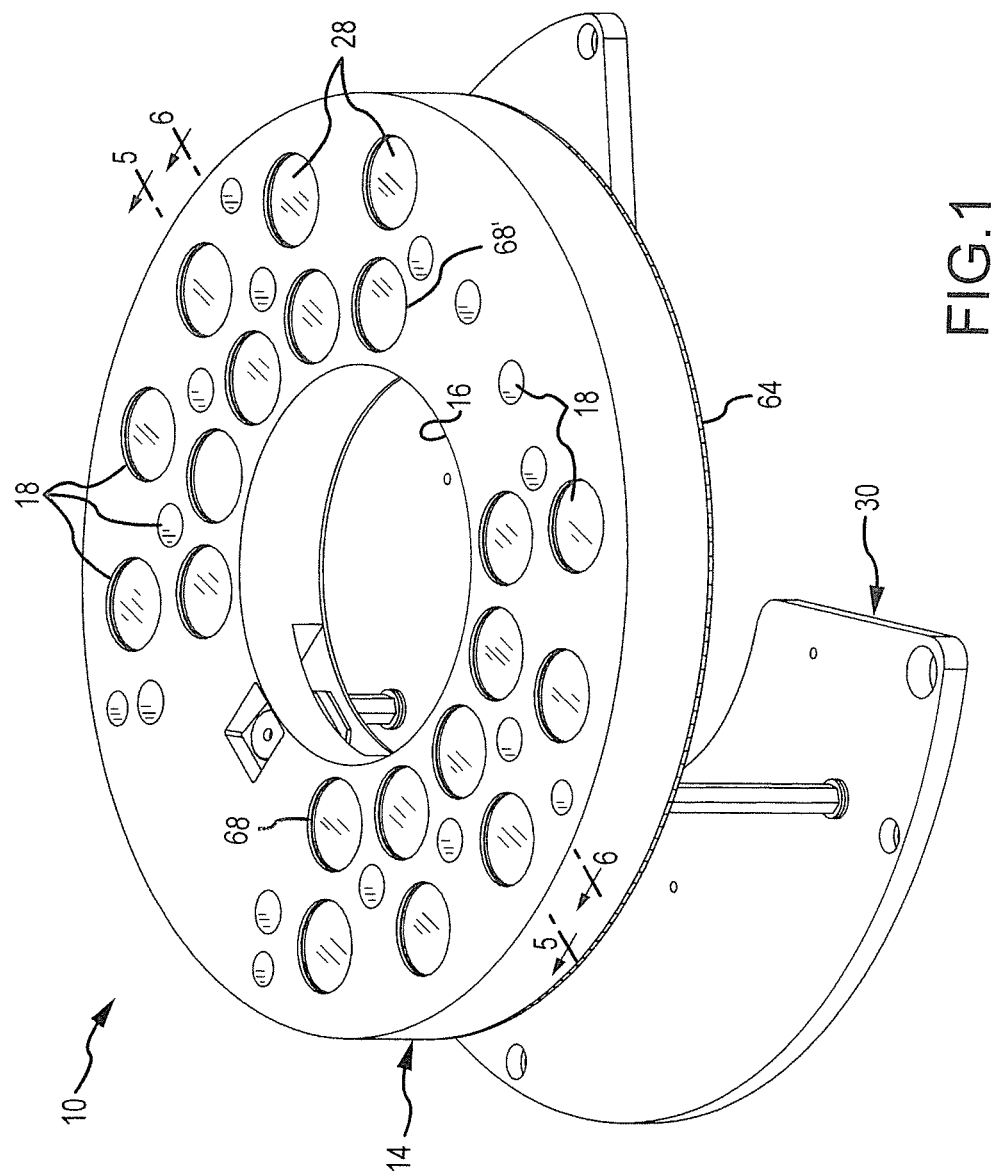
FIG. 1 is a perspective view of an excitation light source assembly according to one embodiment of the present invention.
Figure 2:
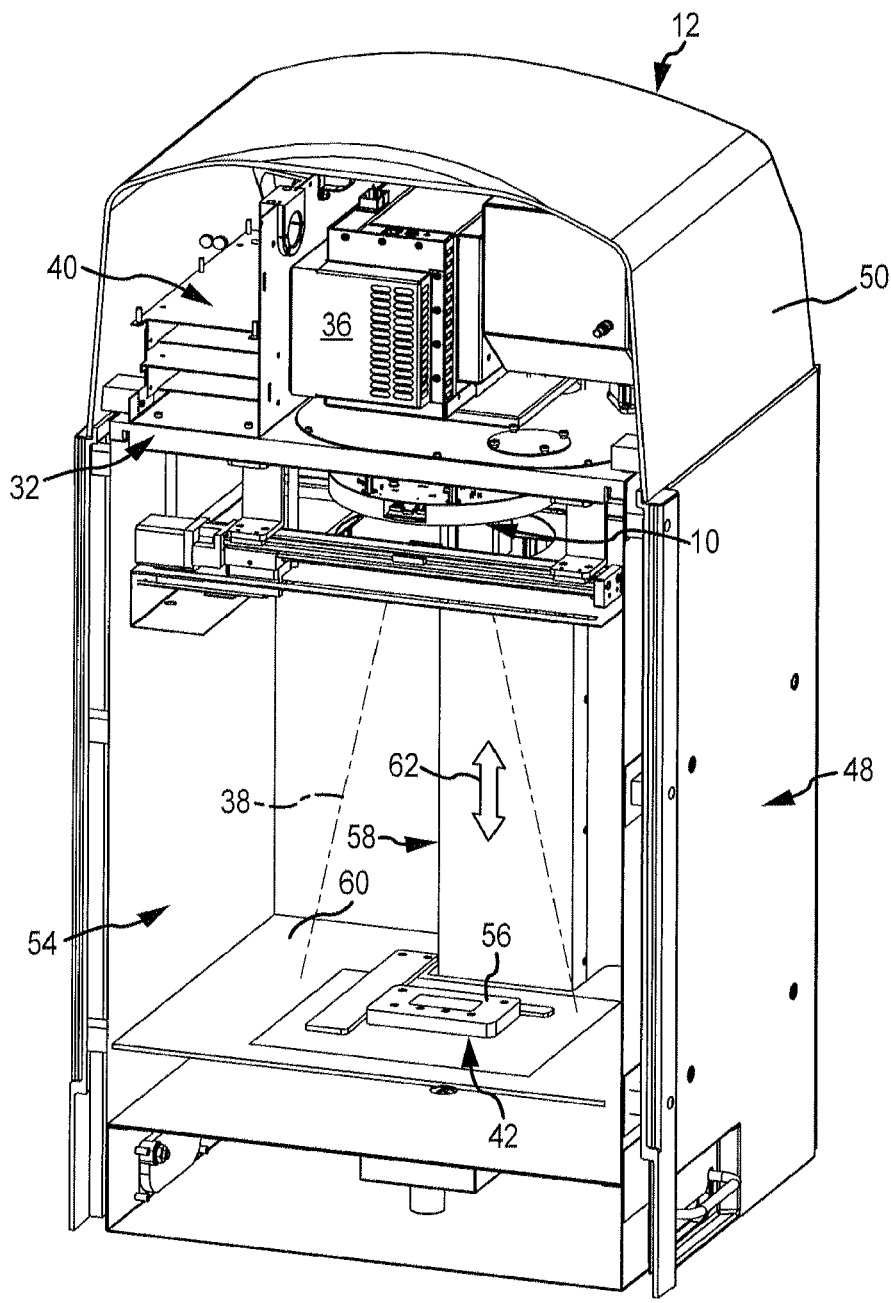
FIG. 2 is a sectional view in perspective of a molecular imaging system having the excitation light source assembly of FIG. 1 provided therein.
Figure 3:
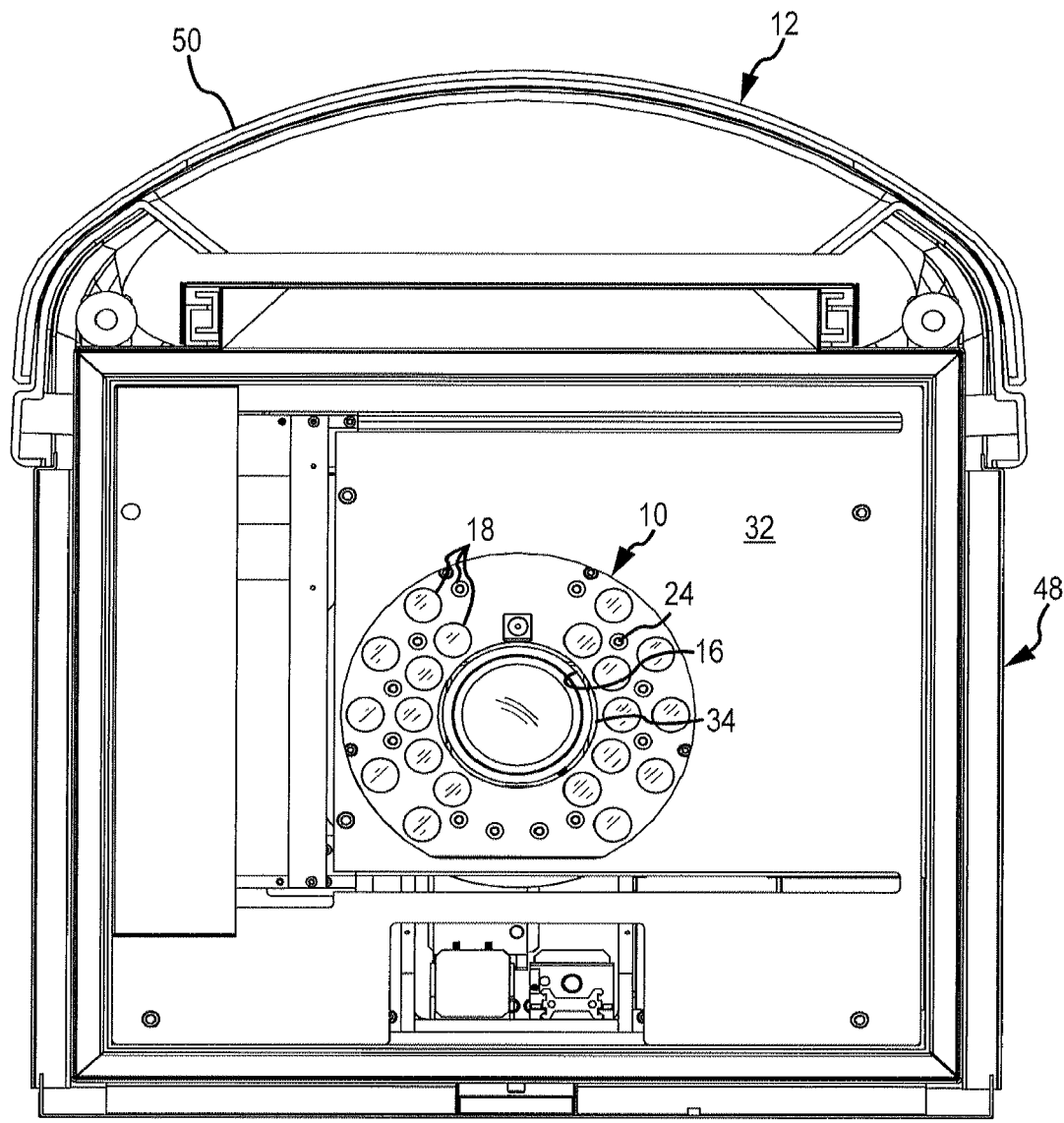
FIG. 3 is a plan view of the support structure of the molecular imaging system of FIG. 2 showing the relative positions of the excitation light source assembly and the lens assembly of the camera.
Figure 4:
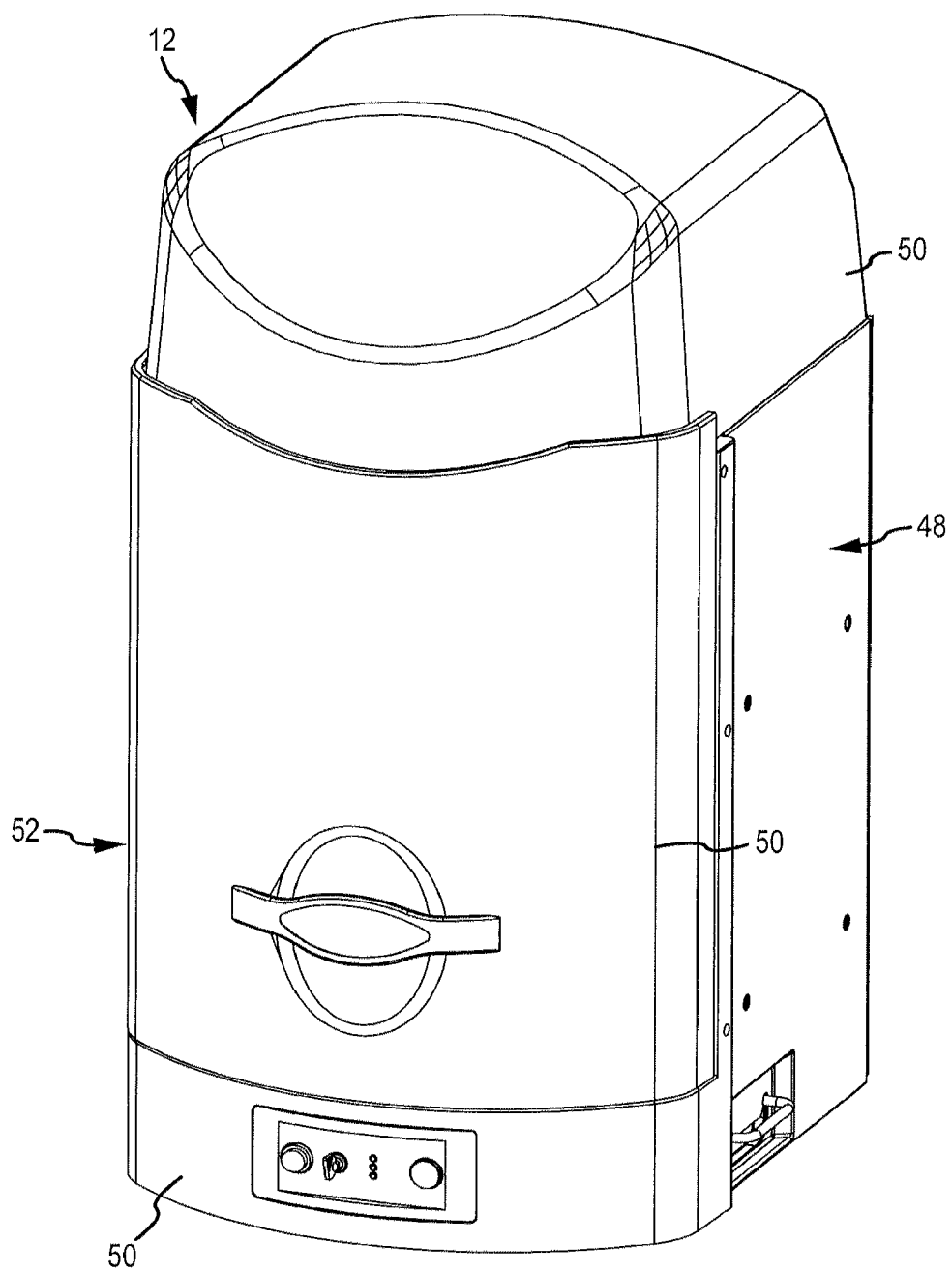
FIG. 4 is an external view in perspective of the molecular imaging system of FIG. 2.
Figure 5:
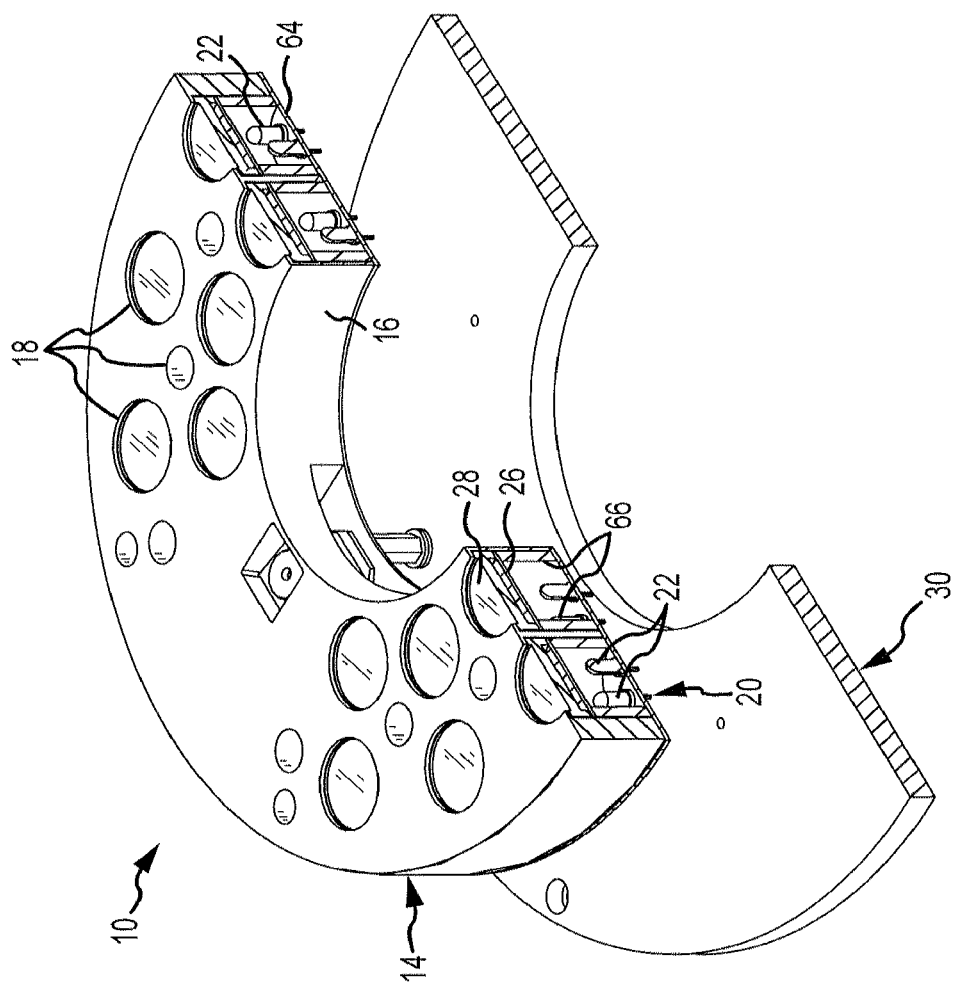
FIG. 5 is a sectional view in perspective of the excitation light source assembly taken along the plane 5-5 of FIG. 1.
Figure 6:
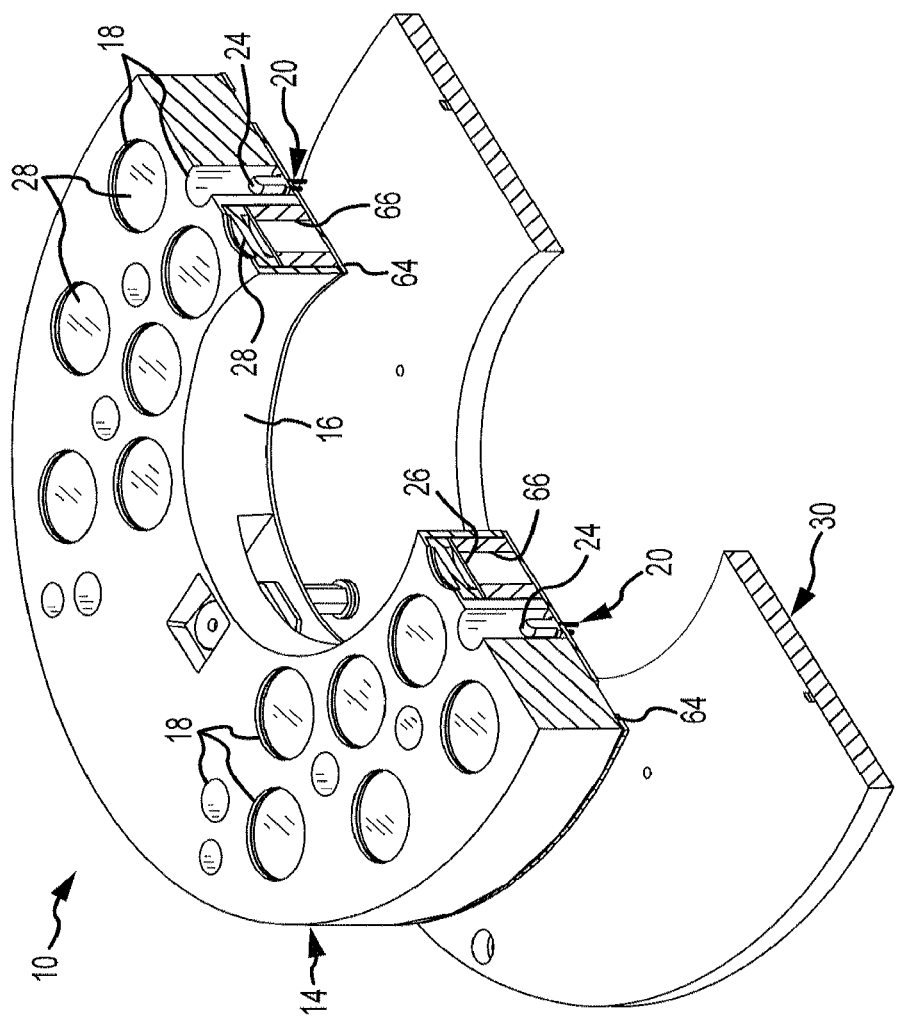
FIG. 6 is a sectional view in perspective of the excitation light source taken along the plane 6-6 of FIG. 1.

One embodiment of an excitation light source assembly 10 is shown in FIGS. 1-3 as it could be used in, or comprise a portion of, a molecular imaging system 12 (also shown in FIG. 4) of the type commonly used in molecular imaging applications. Briefly, the excitation light source assembly 10 may comprise a housing or main body member 14 that defines a central opening 16 therein. The housing or main body member 14 may also define a plurality of lamp receptacles 18 that are arranged around the central opening 16, as best seen in FIGS. 1 and 3. The various lamp receptacles 18 are configured to receive various light sources or lamps 20. More specifically, and as will be described in greater detail below, the light sources or lamps 20 may comprise one or more narrow band light sources 22 and/or one or more broad-band light sources 24, as best seen in FIGS. 5 and 6. Generally speaking, the narrow band light sources 22 are used in fluorescent imaging applications, whereas the broad-band light sources 24 are used in reflected light applications (e.g., to capture a visible light image), although this need not necessarily be the case.

Some of the lamp receptacles 18 may be provided with one or more diffusers 26 and/or one or more filters 28, as best seen in FIG. 5. The diffusers 26 are used to diffuse or spread light produced by the lamps 20, whereas the filters 28 are used to filter or remove light of unwanted or undesirable wavelengths. In a typical application, those lamp receptacles 18 that are provided with narrow band light sources 22 may also be provided with diffusers 26 and filters 28, whereas those receptacles 18 that are provided with broad-band light sources 24 will not be provided with diffusers 26 and filters 28. Alternatively, other arrangements are possible, as will be described herein.

In an embodiment where in the excitation light source assembly 10 is to be used in conjunction with a molecular imaging system 12, it will be generally desirable to provide the excitation light source assembly 10 with the capability to generate or produce excitation light or illumination in a variety of individual bands or colors that extend over a comparatively large wavelength range (e.g., from about 430 nanometers (nm) to about 745 nm). However, other embodiments may extend this range to 800 nm or even 900 nm. In the particular embodiment shown and described herein, the excitation light source assembly 10 is capable of producing or generating ten (10) individual illumination bands or colors having comparatively narrow bandwidths (e.g., in the range of about 30-35 nm), although bandwidths having other ranges may also be used. The ten (10) individual illumination bands or colors (i.e., having relatively narrow bandwidths of about 30-35 nm) thus may cover the large wavelength range of from about 430 nm to about 745 nm. In another embodiment, the wavelength range may be extended to about 900 nm by providing one or more additional illumination bands or colors having wavelengths that extend to 900 nm.

In addition to the ability to provide illumination via one or more narrow illumination bands, the excitation light source assembly 10 may also be used to provide broad-band (e.g., white light) illumination, which may be desirable in certain imaging applications.

In the particular embodiment shown and described herein, each individual illumination band or color is generated or produced by light sources 22 provided in lamp receptacles 18 that are located on opposite sides of the central opening 16. As will be described in greater detail below, this arrangement provides for more even illumination than would otherwise be the case if the individual illumination band or color were provided by only a single lamp receptacle 18.

In an application wherein the excitation light source assembly 10 is used in conjunction with a molecular imaging system 12, the housing or main body member 14 of the excitation light source assembly 10 may be mounted to a base member 30 that, in turn, may be mounted to a suitable support structure 32 associated with the imaging system 12. See FIGS. 2 and 3. More particularly, the excitation light source assembly 10 is mounted to the support structure 32 so that the central opening of main body 14 is substantially aligned with (i.e., concentric to) a lens assembly 34 of a camera 36 associated with the imaging system 12. The arrangement is such that a field of view (represented schematically by lines 38) of camera 36 is substantially unobstructed by the housing 14 and/or central opening 16 of housing 14 of excitation light source assembly 10.

The excitation light source assembly 10 may be operatively connected to a control system 40 (FIG. 2). Control system 40 may be used to operate selected ones of the various light sources 20 (e.g., narrow-band light sources 22 and broadband light sources 24) provided in the excitation light source assembly 10 to provide a desired illumination to an object or specimen 42 located within the field of view 38 of camera 36. Camera 36 may then capture an image of fluorescing material in the object or specimen 42. It should be noted that different fluorescent materials in the specimen 42 may be excited or activated by illuminating the specimen 42 with light of various colors or wavelength bands. In addition, different fluorescent materials in the specimen 42 may fluoresce or emit light of different wavelengths even when illuminated with light of the same color or wavelength band. Images of the specimen 42 produced by light emitted in such different wavelengths may be captured by using an appropriate filter in conjunction with the camera 36.

Figure 7:
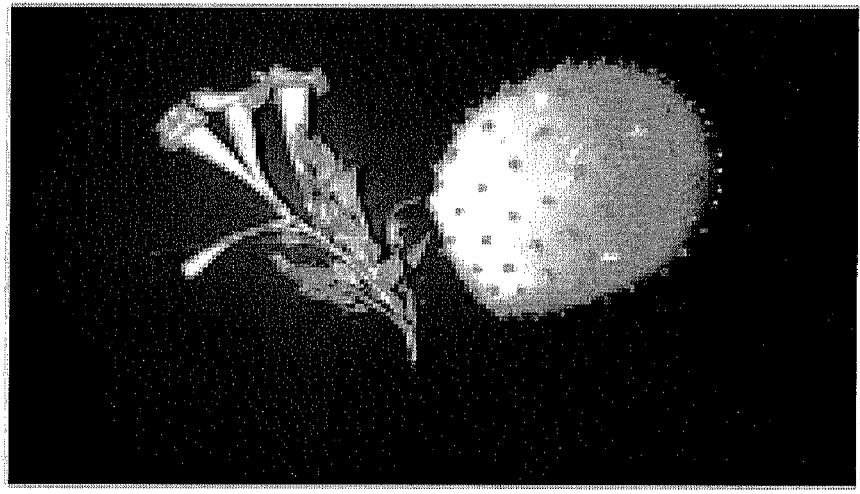
FIG. 7 is fluorescent image of desert flora obtained with excitation light having a wavelength of about 465 nm and observed at a wavelength of about 550 nm.
Figure 8:
FIG. 8 is a fluorescent of the desert flora of FIG. 7 but observed at a wavelength of about 735 nm.

For example, and with reference now to FIGS. 7 and 8, a first fluorescent image 44 of a specimen 42, in this case a cactus pad and flowers, may be obtained by using the control system 40 to activate those light sources 20 that emit light in an individual wavelength band or color that will excite the particular fluorescent material of interest in the specimen 42. In this particular example, the individual wavelength band or color comprised a middle or "center" wavelength of about 465 nm, with a bandwidth of about 30-35 nm. A 550 nm filter was used to capture the image 44 shown in FIG. 7, which was then combined with a visible light image of the specimen 42. The emission at 550 nm reveals the fluorescence of the individual spines of the cactus. However, no fluorescence of the flower appears at this wavelength. In contrast, a second fluorescent image 46 of the specimen 42, depicted in FIG. 8, but captured with a 735 nm filter, reveals emission from the leaves of the flowers as well as from the entire surface of the cactus pad.

A significant advantage of the excitation light source assembly of the present invention is that it may be used to illuminate an object or specimen with light in multiple narrow bands or colors, thereby allowing a single excitation light source assembly to be used in imaging applications involving a wide range of fluorescent materials that are excited over a wide range of wavelengths. Moreover, the excitation light of each individual wavelength band or color may be readily increased and decreased in brightness by controlling the number of light sources in each lamp receptacle that are illuminated or activated at any one time. Still further, the ability of the excitation light source assembly to also provide broadband illumination allows for the ready capture of conventional reflected light images of the object or specimen, which are typically desired in most imaging applications.

Still other advantages are associated with the paring of the lamp receptacles on opposite sides of the central opening, in that such a paring allows for the more even illumination of the object or specimen than would otherwise be the case if the illumination were provided by only a single lamp receptacle.

Still yet other advantages are associated with embodiments having removable lamp receptacles. In such embodiments, the lamp receptacles can be readily removed and replaced in the field, thereby allowing users to conveniently and rapidly tailor the wavelength bands or colors that may be provided by the excitation light source assembly. The present invention also dispenses with the need to provide the illumination via fiber optic bundles, which is expensive and cumbersome. Moreover, such fiber optic bundles must also be carefully selected so that they do not contain materials or elements that themselves would fluoresce in use.

Having briefly described one embodiment of the excitation light source assembly of the present invention, as well as some of its more significant features and advantages, various exemplary embodiments of the excitation light source assembly will now be described in detail. However, before proceeding with the description, it should be noted that while the particular embodiments are shown and described herein as they could be used to provide illumination over certain wavelength ranges and in certain narrow illumination bands or colors having certain bandwidths, the particular wavelength ranges, numbers of illumination bands, as well as the bandwidths of the illumination bands may be varied depending on the any of a wide range of factors, including the requirements of the particular application. Consequently, the present invention should not be regarded as limited to the particular examples, ranges, wavelength bands, and applications shown and described herein.

Referring back now to FIGS. 1-4, an excitation light source assembly 10 according to one embodiment of the present invention is shown and described herein as it may be used in conjunction with a molecular imaging system 12 of the type commonly used in the molecular imaging field. In the particular embodiment shown and described herein, the imaging system 12 may comprise a generally rectangularly-shaped chassis or main enclosure 48 configured to house and support the various components and subsystems required to perform various types of molecular imaging processes. In addition, the main enclosure 48 also may be provided with various external finish panels 50 that cover or overlay the underlying chassis or main enclosure structure 48. In the particular embodiment shown and described herein, the imaging system 12 is designed or configured to be connected to separate computer system (not shown) to allow a user to operate the imaging system 12 and view images produced by the imaging system 12 on a suitable display system (also not shown).

The main enclosure 48 of imaging system 12 may be provided with an access door 52 that can be moved vertically between a closed position (shown in FIG. 4) and an opened position (not specifically illustrated in the drawing figures) to allow the user to access an imaging compartment or chamber 54 defined by the main enclosure 48, as best seen in FIG. 2. The imaging compartment 54 is sized to receive one or more objects or specimens 42 to be imaged. Objects or specimens 42 suitable for use with the imaging system 12 include samples that may be provided in a well plate 56, as well as living organisms (not shown). Other types of objects or specimens 42 may be imaged for other purposes as well, as would become apparent to persons having ordinary skill in the art after having become familiar with the teachings provided herein.

Referring now primarily to FIG. 2, the imaging system 12 also may include an imaging system sub-assembly 58 having an object platform or stage 60, as well as a mounting or support structure 32. The object platform 60 is moveably mounted to the sub-assembly 58 so that the object platform 60 can be moved vertically toward and away from the support structure 32, i.e., generally in the direction indicated by arrows 62. The support structure 32 is configured to receive camera 36, control system 40, as well as various other components and systems required for operation of the imaging system 12. However, because such various other components and systems that may be required or desired for the operation of the imaging system 12 are not required to understand or practice the present invention, such additional components and systems will not be described in further detail herein.

The excitation light source assembly 10 may comprise a housing or main body 14 that defines a central opening 16 therein, as best seen in FIG. 1. The housing or main body member 14 may be mounted to a base member 30 to allow the excitation light source assembly 10 to be readily mounted to the support structure 32 of the imaging system 12, as best seen in FIGS. 2 and 3. As mentioned above, the excitation light source assembly 10 is mounted to the support structure 32 so that the central opening 16 of main body 14 is substantially aligned with the lens assembly 34 of camera 36. The arrangement is such that the field of view 38 of camera 36 is substantially unobstructed by the housing 14 and/or central opening 16 of housing 14.

Referring now primarily to FIGS. 3, 5, and 6, the main body member 14 of excitation light source assembly 10 also defines a plurality of lamp receptacles 18 therein that are arranged around the central opening 16. Each of the lamp receptacles 18 is sized or configured to receive one or more light sources or lamps 20 (FIGS. 5 and 6). In particular, the large diameter lamp receptacles 18 may be sized to receive one or more narrow-band light sources 22, as best seen in FIG. 5, whereas the small diameter lamp receptacles 18 may be sized to receive a single broad-band light source 24, as best seen in FIG. 6.

The various lamp receptacles 18 may be provided at locations on the main body member 14 so as to provide substantially uniform illumination to the object or specimen 42 provided on the imaging platform or stage 60. In the particular embodiment shown and described herein, the main body member 14 is provided with twenty (20) large diameter lamp receptacles 18, each of which is provided with a plurality of narrow-band light sources 22 and, optionally, diffusers 26, and filters 28. Moreover, and as will be described in further detail below, a given large diameter lamp receptacle 18 (such as receptacle 68),may be matched with a counterpart large diameter receptacle 18 (such as receptacle 68') on the opposite side of central opening 16. See FIG. 1. Both the receptacle 68 and its counterpart receptacle 68' may be configured to emit light of the same color or wavelength range. Thus, when energized, each such receptacle 68 and counterpart receptacle 68' will emit light of the same color or wavelength range. Because each such receptacle 68 and counterpart receptacle 68' are located on opposite sides of the central opening 16, the specimen 42 will be more evenly illuminated with this arrangement than would otherwise be the case if the light were emitted only by a single receptacle 18.

As briefly described above, each of the small diameter receptacles 18 may be provided with a single broad-band light source 24. The various small diameter receptacles 18 also may be provided in spaced-apart relation around the central opening 16 of body member 14 in order to provide substantially uniform illumination of the object 42 provided on the stage 60 when the broad-band light sources 24 are energized.

The housing or main body member 14 may be fabricated from any of a wide range of materials, such as metals or plastics, that would be suitable for the intended application. Generally speaking, it will be desirable to use a material that will not fluoresce in response to the illumination provided by the various light sources 20 provided therein, as such fluorescence of the material comprising the main body member 14 will degrade the performance of the imaging system 12. By way of example, in one embodiment, the housing or main body member 14 is fabricated from a polyoxymethylene thermoplastic material, such as Delrin®. Alternatively, other materials may also be used, as would become apparent to persons having ordinary skill in the art after having become familiar with the teachings provided herein. Consequently, the present invention should not be regarded as limited to a main body member 14 that is fabricated from any particular material.

With reference now primarily to FIG. 5, each of the large diameter lamp receptacles 18 defined by the housing 14 of the excitation light source assembly 10 is sized or configured to receive at least one, and preferably three (3) narrow-band light sources 22 (only two of which are shown in FIG. 5). As will be described in greater detail below, the individual narrow-band light sources 22 may be individually activated by control system 40 to provide illumination of three (3) different intensity levels by activating various ones of the three narrow-band sources 22 provided to each lamp receptacle. In contrast, each of the small diameter lamp receptacles 18 may be sized to receive a single broad-band light source 24. However, other arrangements are possible, as would become apparent to persons having ordinary skill in the art after having become familiar with the teachings provided herein. Consequently, the present invention should not be regarded as limited to any particular configuration with respect to the number of light sources 20 that may be provided to each lamp receptacle 18.

The various light sources 20, e.g., comprising narrow-band light sources 22 and broad-band light sources 24, may be mounted to a circuit board 64 which, in turn, may be mounted or affixed to the main body 14, as best seen in FIGS. 1, 5, and 6. Circuit board 64 provides a means for physically supporting the various light sources 20 within the lamp receptacles 18 and for electrically connecting the light sources 20 to the control system 40. Circuit board 64 may also be provided with any of a wide range of ancillary systems and devices, such as light source drive circuits and connectors, to allow the light sources 20 to be activated by control system 40. However, because such devices and systems are well-known in the art and could be readily provided by persons having ordinary skill in the art after having become familiar with the teachings provided herein, the circuit board 64 that may be utilized in one embodiment of the present invention will not be described in further detail herein.

Each narrow-band light source 22 is suitable for producing excitation light having a wavelength band or color that comprises at least the wavelength or wavelengths required to excite or activate fluorescence in the particular material or specimen 42 to be imaged or studied. In addition, because it will be desirable to use the imaging system 12 to image a wide range of fluorescent materials, various ones of which may require excitation light having different colors or wavelength bands, in one embodiment, each of the larger diameter lamp receptacles 18 defined by the housing 14 will hold at least one, and preferably three (in one embodiment), narrow-band light source 22 that emits light having wavelengths (i.e., a wavelength band) that is slightly different from the wavelengths produced by the other narrow-band light sources 22 provided in others of the larger diameter lamp receptacles 18. Stated another way, the various lamp receptacles 18 may emit light of different colors. In this manner, then, the single housing 14 of excitation light source assembly 10 can be used to produce excitation light having wavelengths across any desired wavelength range.

In addition, and as was also mentioned above, each of the larger diameter lamp receptacles 18 (e.g., lamp receptacle 68, FIG. 1) may be paired with a counterpart receptacle (e.g., lamp receptacle 68') on the opposite side of the central opening 16 in order to provide more even illumination of the specimen 42 provided on the imaging platform or stage 60. For example, if a particular lamp receptacle 68 is provided with a narrow-band light source 22 that is capable of emitting light having middle or center wavelength of about 465 nm, then its counterpart receptacle 68' should also be provided with a narrow-band light source 22 having a middle or center wavelength of about 465 nm.

In the particular embodiment shown and described herein, the excitation light source assembly 10 is capable of emitting excitation light in a plurality of individual bands or colors over a wavelength range from about 430 nm to about 745 nm. Therefore, it will be generally desirable to use for each light source 20 a comparatively narrow-band light source 22 that emits light having wavelengths over a fairly narrow-band. By way of example, narrow-band light sources 22 having bandwidths in the range of about 30-35 nm can be used to advantage in the present invention. If such narrow-band light sources 22 are used, ten (10) such narrow-band light sources 22, properly selected, will be sufficient to cover the exemplary wavelength range. In accordance with this objective, then, the main body member 14 is provided with twenty (20) large diameter receptacles 18 that are arranged in ten pairs of two on opposite sides of the central opening 16. The corresponding receptacle pairs (e.g., 68 and 68', FIG. 1) are then provided with narrow-band light sources 22 of the same wavelengths so that the excitation light source assembly 10 is capable of providing illumination in ten different narrow-band wavelength ranges or colors.

Alternatively, another embodiment of the invention may produce light having a wavelength of 800 nm by providing one or more light sources 22 capable of producing light having wavelengths of around 800 nm. In still another embodiment, the range could be extended to wavelengths of 900 nm or even longer by providing the excitation light source assembly 10 with light sources 22 capable of producing light having wavelengths of around 900 nm.

Each narrow-band light source 22 may comprise a light emitting diode (LED) that emits light in the desired wavelength band, and ideally, with the desired bandwidth (e.g., of about 30-35 nm). Light emitting diodes having such narrow bandwidths (e.g., about 30-35 nm) along the desired wavelength range (e.g., 430 nm to about 745 nm) are readily commercially available and can be used as the narrow-band sources 22. However, it should be noted that suitable LEDs that emit or produce light in each of the desired wavelength bands may not be available. If so, it may be necessary to use broader-band LEDs, i.e., that emit light having wavelengths outside the desired wavelength range. If so, such LEDs or broad-band light sources may be used in combination with a filter element 28 to filter or remove the undesired wavelengths, as will be described in greater detail below.

Regardless of the particular light source 22 that may be used, it is also generally preferred, but not required, to provide a diffuser 26 within each lamp receptacle 18. The diffuser 26 may be provided at any convenient position within lamp receptacle 18. In one embodiment, diffuser 26 is located at a position immediately adjacent the light source 20, as best seen in FIG. 5. A sleeve 66 provided in the lamp receptacle 18 may be used to support diffuser 26, although other arrangements are possible. As its name implies, the diffuser 26 diffuses or spreads light produced by the light source 20, thereby generally providing for more even illumination than would be provided by the light source 22 alone.

The diffuser 26 may comprise any of a wide range of optical diffusers that are now known in the art or that may be developed in the future that are or would be suitable for the particular application. However, because optical diffusers are well-known in the art and could be readily provided by persons having ordinary skill in the art after having become familiar with the teachings provided herein, the particular diffusers that may be used in one embodiment of the invention will not be described in further detail herein.

As mentioned above, the light output characteristics of the various light sources 20 (e.g., LEDs) that may be utilized in the excitation light source assembly 10 may be such that it may be required, or at least desirable, to further limit the wavelength range of excitation light produced by each light source 20. This may be the case regardless of whether the particular light source 20 involved is a narrow-band light source 22. Accordingly, in one embodiment, each of the large diameter lamp receptacles 18 (e.g., containing or housing the narrow-band light sources 22) may also be provided with a filter element 28. Filter element 28 may remove or filter undesired wavelengths produced by the light source 20, regardless of whether the light source 20 comprises a narrow-band light source 22. In the particular embodiment shown and described herein, each such filter may be positioned adjacent the diffuser 26, as best seen in FIG. 5, although other arrangements are possible.

In the particular embodiment shown and described herein, each filter element 28 may comprise a "notch" type filter having a relatively narrow wavelength bandpass range of about 30 nm around the desired center wavelength or color. Such notch type filters are available over a wide range of wavelengths or colors. In one embodiment of the invention, a separate notch filter 28 is provided for each light source 22, and the notch filter wavelength is selected as appropriate for the particular light source 22 with which it is paired. Thus, when individually activated, each light source/filter combination will emit excitation light having a bandwidth of about 30 nm at a desired color or wavelength band within the desired overall wavelength range (e.g., from about 430 nm to about 745 nm).

Referring now primarily to FIG. 6, the excitation light source assembly 10 may also be provided with a plurality of small diameter lamp receptacles 18 therein that are sized to receive a broad-band light source 24. In the particular embodiment shown and described herein, each small diameter lamp receptacle 18 receives a single broad-band light source 24, although other embodiments may be provided with a plurality of broad-band light sources 24 for each receptacle 18. Broad-band light source 24 may comprise any of a wide range of broad-band light sources now known in the art or that may be developed in the future that are, or would be, suitable for the intended application. By way of example, in one embodiment, each broad-band light source 24 may comprise a "white" LED of the type that are readily commercially available. In another embodiment, one or more of the broad-band light sources 24 may be mounted at other locations within the imaging system 12.

Each of the various light sources 20, i.e., comprising narrow-band sources 22 and broad-band sources 24, provided in the various lamp receptacles 18 defined by the housing 14 may be operatively connected to a control system 40 (FIG. 2) via the circuit board 64. Control system 40 may be used to operate or energize the various light sources 20 to turn them on and off. In one embodiment, each of the various light sources 20 (i.e., comprising narrow-band sources 22 and broad-band sources 24) may be individually controlled so that a single light source 20, emitting excitation light in a desired wavelength band or color, may be used to excite the desired fluorescent material contained in the object or specimen 42 being studied. Alternatively, other arrangements are possible. For example, in another embodiment, the control system 40 may operate two or more light sources 20 simultaneously.

The excitation light source 10 may be operated as follows to capture a fluorescent image of a specimen 42, for example a cactus pad and flowers. Once the specimen 42 has been properly positioned on the platform or stage 60 and the imaging system 12 otherwise prepared for operation, the control system 40 may operate selected ones of the various light sources 20 (e.g., narrow-band light sources 22 and broad-band light sources 24) to illuminate the specimen 42 with a desired wavelength band or color. Camera 36 may then capture an image of fluorescing material in the object or specimen 42. As described earlier, different fluorescent materials in the specimen 42 may be excited or activated by illuminating the specimen 42 with light of various colors or wavelength bands. In addition, different fluorescent materials in the specimen 42 may fluoresce or emit light of different wavelengths even when illuminated with light of the same color or wavelength band. Images of the specimen 42 produced by light emitted in such different wavelengths may be captured by using an appropriate filter in conjunction with the camera 36.

For example, and with reference now to FIGS. 7 and 8, a first fluorescent image 44 of specimen 42 may be obtained by using the control system 40 to activate those light sources 20 that emit light having a middle or center wavelength of about 465 nm (and with a bandwidth of about 30-35 nm). Certain materials contained within the specimen 42 will fluoresce in response to this excitation illumination. However, the materials may not all fluoresce or emit light of the same wavelength. Different materials will fluoresce or emit light of different wavelengths, as is known. The particular fluorescent image 44 depicted in FIG. 7 was captured with a 550 nm filter adjacent the camera 36 and is shown combined with a visible light image of the specimen 42. The emission at 550 nm reveals the fluorescence of the individual spines of the cactus. However, no fluorescence of the flower appears at this wavelength. In contrast, the second fluorescent image 46 depicted in FIG. 8, but captured with a 735 nm filter, reveals emission from the leaves of the flowers as well as from the entire surface of the cactus pad.

Figure 9:
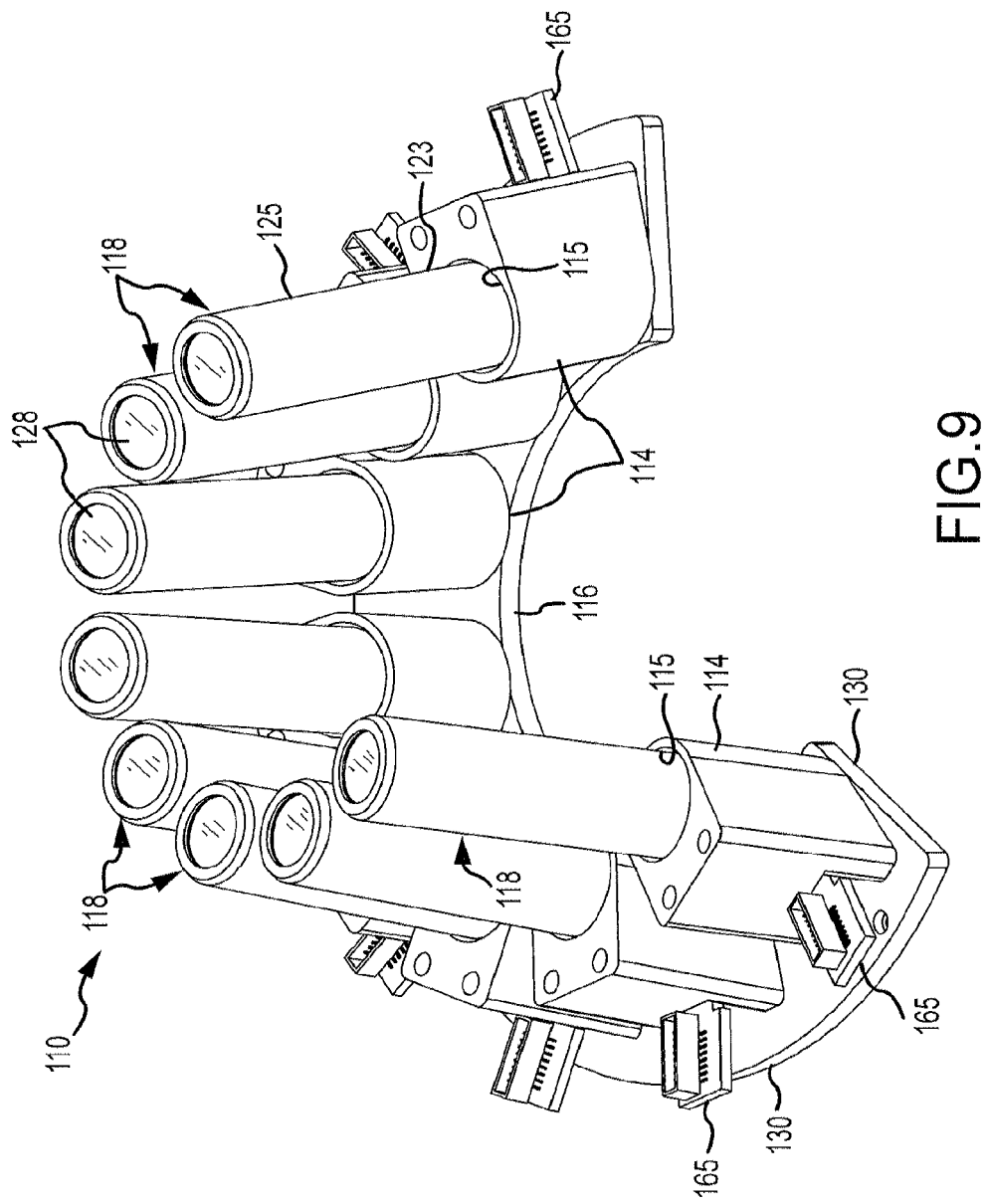
FIG. 9 is a perspective view of a second embodiment of an excitation light source assembly having a plurality of removable lamp modules.
Figure 10:
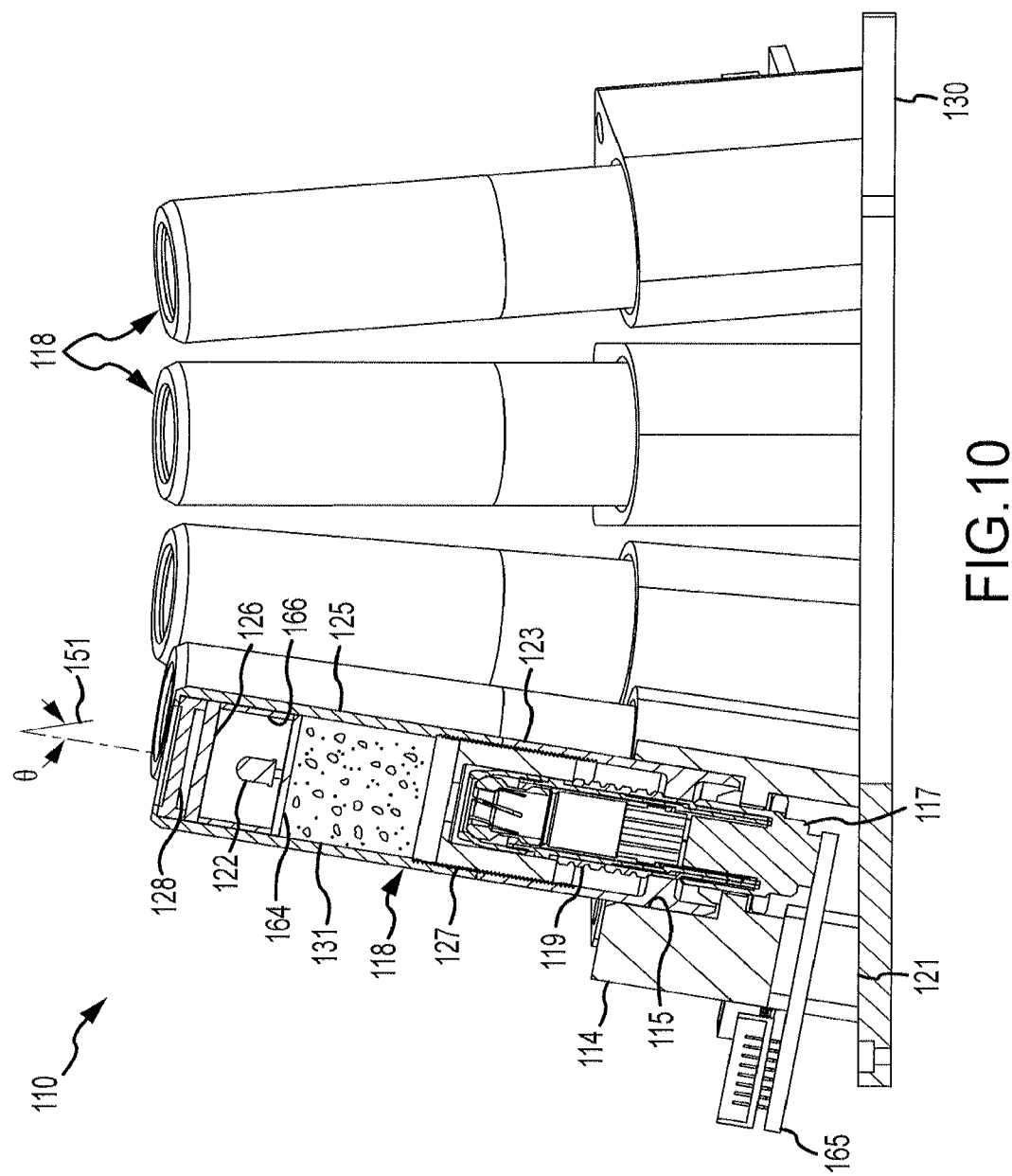
FIG. 10 is a sectional view in elevation of one of the plurality of removable lamp modules of the second embodiment of the excitation light source assembly of FIG. 9.
Figure 11:
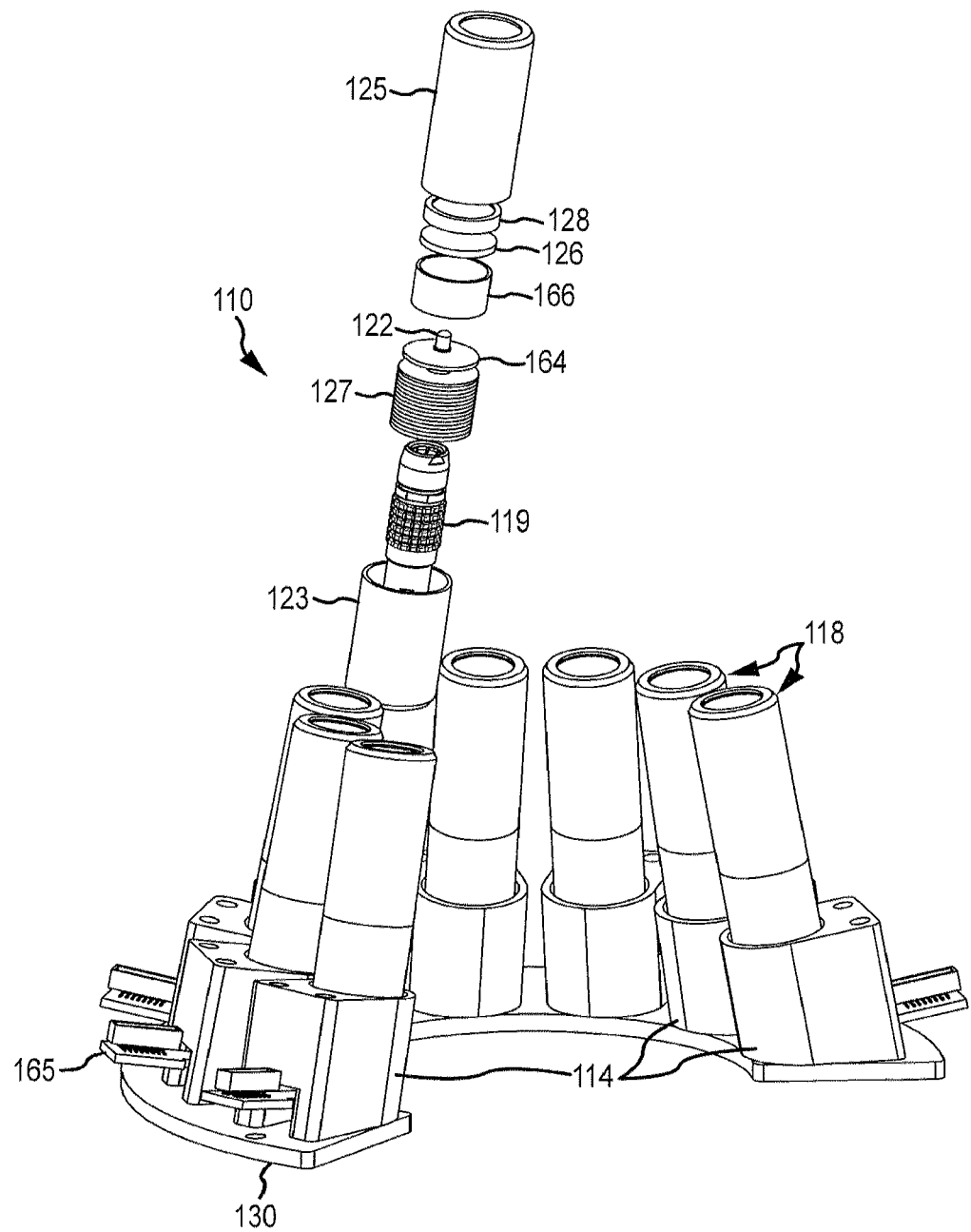
FIG. 11 is an exploded perspective view of one of the removable lamp modules of the second embodiment of the excitation light source assembly of FIG. 9.

Other variations and configurations are possible for the excitation light source according to the present invention. For example, a second embodiment 110 of an excitation light source assembly according to the teachings of the present invention is illustrated in FIGS. 9-11. The second embodiment 110 differs from the first embodiment 10 in that the second embodiment 110 comprises a plurality of lamp receptacles 118 that are removable from corresponding main bodies 114. The removable lamp receptacles 118 allow the excitation light source 110 to be readily configured (and reconfigured) to produce light of any desired wavelength band or color by simply removing one or more of the lamp receptacles 118 and replacing it or them with another lamp receptacle 118 that configured to produce light in the desired wavelength band or color.

The second embodiment 110 may comprise a base member 130 to which are mounted a plurality of main bodies 114. In the particular embodiment illustrated in FIGS. 9-11, the base member 130 comprises a C-shaped member having a central opening 116. Alternatively, the base member 130 could comprise other shapes and configurations, such as the circular shape of the first embodiment 110. The overall configuration of the C-shaped base member 130 is such that the central opening 116 thereof will be substantially aligned with the lens assembly 34 of camera 36 when mounted to the support structure 32 of imaging system 12. See FIGS. 2 and 3. As was the case for the first embodiment 10, the arrangement of the second embodiment 110 is such that the field of view 38 of camera 36 is substantially unobstructed by the central opening 116 of base member 130, as well as the various light receptacles 118 associated with excitation light source assembly 110.

With reference now primarily to FIG. 10, each main body 114 may be substantially identical to the others and may comprise an opening 115 therein sized to receive the corresponding removable lamp receptacle 118. Main body 114 may also be configured to receive a connector assembly 117 that is sized to removably receive a mating portion 119 provided in the removable lamp receptacle 118. The connector assembly 117 and mating portion 119 provide physical and electrical engagement with the removable lamp receptacle 118. Connector assembly 117 may be electrically connected to an electrical connector assembly 165 provided in the main body 114. See also FIG. 9.

In the particular embodiment shown and described herein, each main body 114 has an angled base portion 121 so that the each lamp receptacle 118 is angled inward, toward the central axis 151 of the housing 114, by an angle θ, as best seen in FIG. 10 (central axis 151 is shown in a displaced position in FIG. 10 for clarity). Such an arrangement allows the excitation light produced by the various lamp receptacles 118 to roughly converge at a point on the image platform or stage 60 where the specimen 42 is to be located during the imaging operation. Alternatively, other arrangements for aiming or directing the lamp receptacles 118, thus excitation light emitted thereby, could also be used, as would become apparent to persons having ordinary skill in the art after having become familiar with the teachings provided herein.

The base member 130 and each of the main bodies 114 may be fabricated from any of a wide range of materials (e.g., metals and plastics) that would be suitable for the intended application. By way of example, in one embodiment the base member 130 may comprise aluminum. Each of the main bodies 114 may be fabricated from a polyoxymethylene thermoplastic material, such as Delrin®. Alternatively, other materials may also be used.

Connector assembly 117 and its mating portion 119 may comprise any of a wide range of connector assemblies that are now known in the art or that may be developed in the future that are, or would be, suitable for the particular application. However, by way of example, in one embodiment, connector assembly 117 and its mating portion 119 may comprise a type "FGG" connector assembly available from LEMO USA, Inc. of Rohnert Park, Calif. Alternatively, other types of connectors may be used.

Referring now to FIGS. 10 and 11 simultaneously, each lamp receptacle 118 may be substantially identical to the others and may comprise first and second barrel sections 123 and 125 that may be connected or joined together by a threaded nipple or sleeve section 127. Sleeve section 127 is also configured to receive mating connector portion 119, as best seen in FIG. 10. The upper barrel section 125 may be configured to receive one or more narrow-band light sources 122 (only a single narrow-band light source 122 is illustrated in FIGS. 10 and 11), which may be mounted to a circuit board 164 that is electrically connected to mating connector portion 119 via wires (not shown) or other suitable means. Barrel section 125 may also be configured to receive a diffuser 126 and/or a filter 128, as best seen in FIG. 11. A sleeve 166 may be used to position the diffuser 126 and/or filter 128 with respect to the light source 122. A foam spacer 131 or other elastomeric material may be provided between circuit board 164 and sleeve 127, as best seen in FIG. 10.

The upper and lower barrel sections 123 and 125 may be fabricated from any of a wide range of materials, such as metals or plastics, that would be suitable for the intended application. Consequently, the present invention should not be regarded as limited to any particular material. However, by way of example, in one embodiment, the upper and lower barrel sections 123 and 125 are fabricated from aluminum. The aluminum may be provided with a suitable non-reflective coating.

Figure 12:
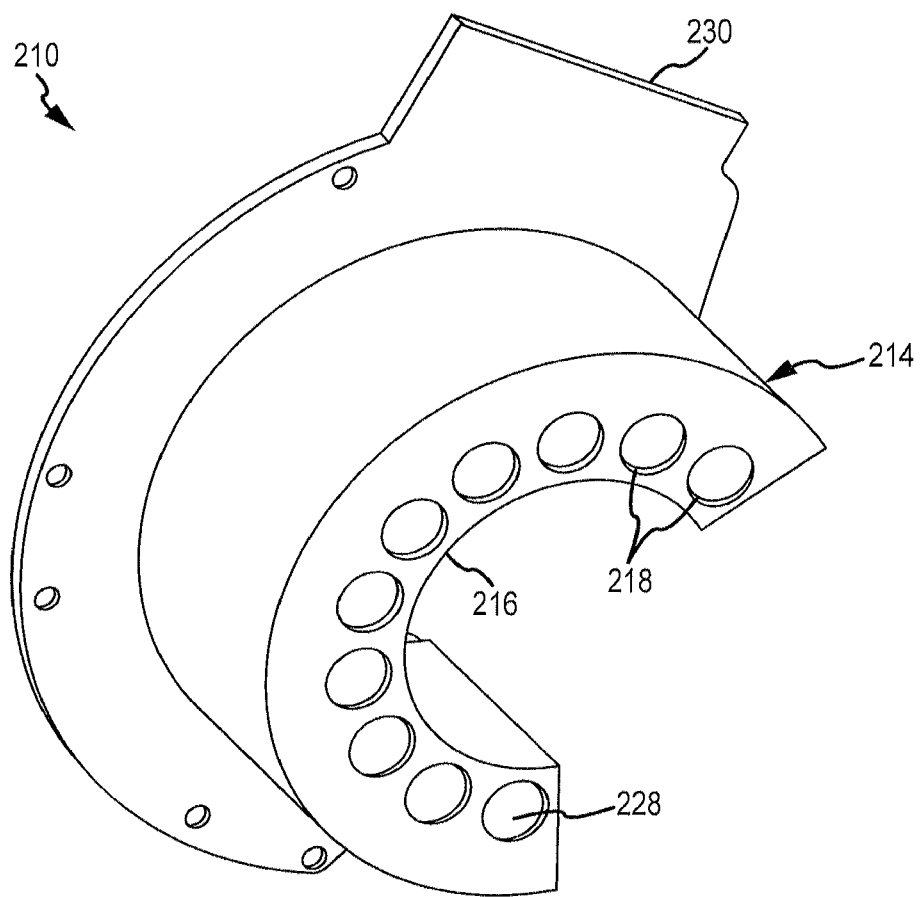
FIG. 12 is a perspective view of a third embodiment of an excitation light source assembly.

Still other variations are possible. For example, and with reference now to FIGS. 12 and 13, a third embodiment 210 of the excitation light source assembly may comprise a "C"-shaped housing or main body 214 that defines a central opening 216. The housing 214 also defines a plurality of lamp receptacles 218 that are arranged around the central opening, as best seen in FIG. 12. The housing 214 of the excitation light source assembly 210 is also configured to be mounted to the support structure 32 of imaging system 12, so that the lens assembly 34 of camera 36 is generally concentric with the central opening 216 defined by the housing 214. See FIGS. 2 and 3. As was the case for the other embodiments, the arrangement is such that the field of view 38 of the camera 36 is substantially unobstructed by the housing 214 and/or central opening 216 of housing 214 of the excitation light source assembly 214.

Figure 13:
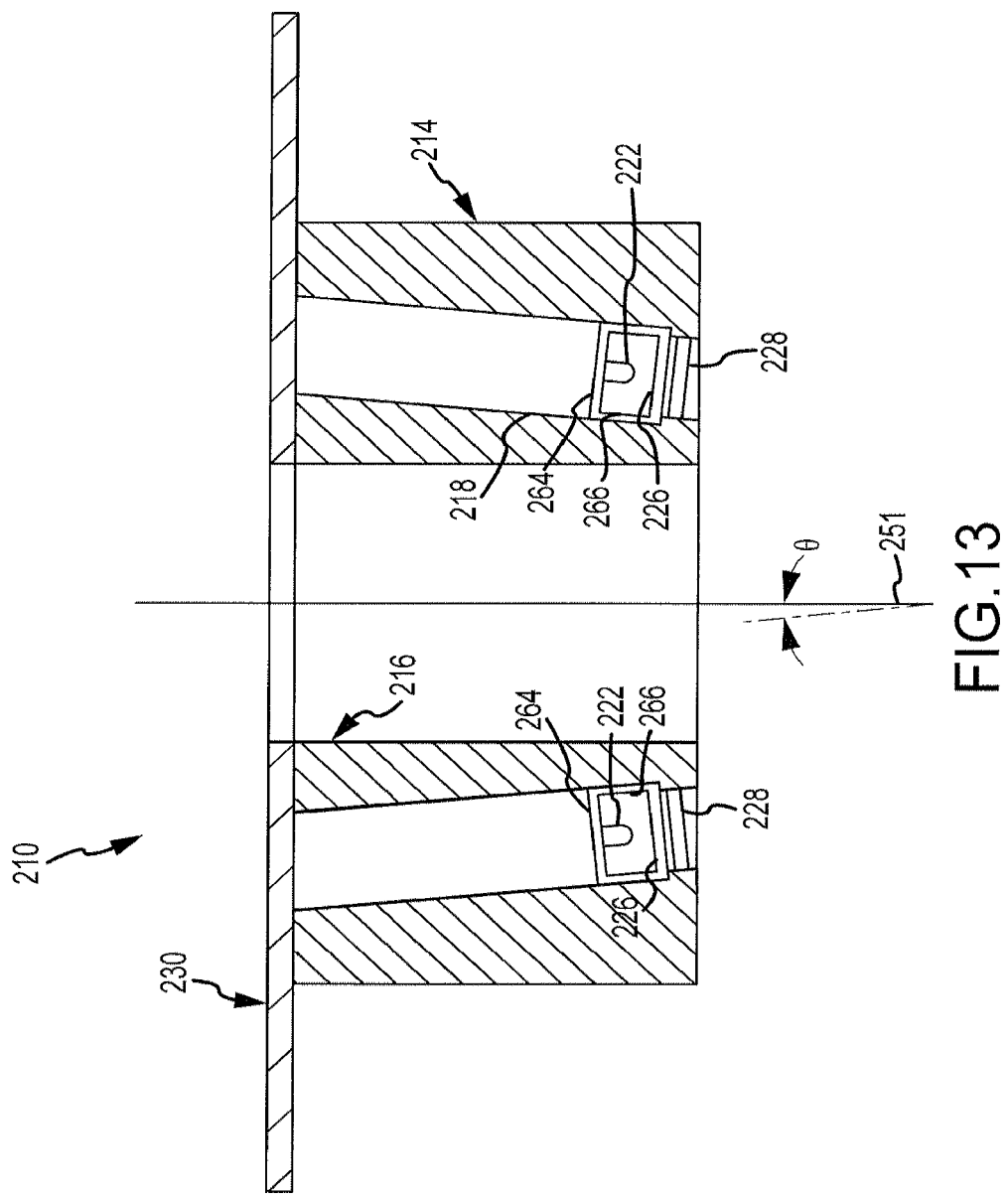
FIG. 13 is a sectional view in elevation of the excitation light source assembly of FIG. 12.

Referring now to FIG. 13, each of the lamp receptacles 218 may be provided narrow-band light source 222 that, in one embodiment, may be mounted to a circuit board 266. A diffuser 226 may also be positioned within each of the lamp receptacles 218, generally at a position adjacent the light source 222. Each diffuser 226 diffuses light produced by the corresponding light source 222 and may be held in position by a sleeve 266. As was the case for the other embodiments, each lamp receptacle 218 may also be provided with a filter 228, if desired or required, to remove or filter any undesired light wavelengths that may be produced by the light source 222.

The C-shaped housing 214 of the excitation light source assembly 210 allows each of the lamp receptacles 218 provided therein to be conveniently angled (i.e., by an angle θ with respect to the central axis 251 of housing 214), so that light from the light sources 222 may be directed to a desired area within the field of view 38 of camera 36.

The housing 214 for the excitation light source assembly 210 may be fabricated from any of a wide range of materials, such as metals or plastics, that would be suitable for the intended application. Consequently, the present invention should not be regarded as limited to housings made from any particular materials. However, by way of example, in one embodiment, the housing is fabricated as a single piece from any of a polyoxymethylene thermoplastic material, e.g., Delrin®.

Having herein set forth preferred embodiments of the present invention, it is anticipated that suitable modifications can be made thereto which will nonetheless remain within the scope of the invention. The invention shall therefore only be construed in accordance with the following claims:

The invention claimed is:

1. An excitation light source assembly, comprising:
a housing defining a central opening therein and a plurality of lamp receptacles surrounding the central opening, said housing being mountable to a support structure so that the central opening is aligned with a camera also mounted to the support structure so that a field of view of the camera is unobstructed by said housing;
a light source positioned within each of the plurality of lamp receptacles, wherein at least one of said light sources comprises a narrow-band light source; and
a diffuser positioned within at least some of the plurality of lamp receptacles, each of said diffusers diffusing light produced by each of said light sources; and
a control system operatively connected to each of said light sources said control system operating selected ones of said light sources to provide a desired excitation illumination to an object within the field of view of said camera, the object fluorescing in response to the excitation illumination provided by said light sources.

2. The excitation light source assembly of claim 1 wherein said narrow-band light source emits light having a bandwidth of about 35 nm.

3. The excitation light source assembly of claim 2 wherein said at least one narrow-band light source comprises a light emitting diode.

4. The excitation light source assembly of claim 1, further comprising at least one filter positioned adjacent at least one diffuser in at least one of the lamp receptacles defined by said housing.

5. The excitation light source assembly of claim 4, wherein said at least one filter comprises a notch filter having a wavelength bandpass range of about 30 nm.

6. The excitation light source assembly of claim 1, wherein at least one of the light sources comprises a broad-band light source.

7. The excitation light source assembly of claim 1, wherein at least some of said plurality of lamp receptacles comprise opposed pairs of lamp receptacles on opposite sides of said central opening, each opposed pair of lamp receptacles producing light of the same color.

8. The excitation light source assembly of claim 7, further comprising ten opposed pairs of lamp receptacles on opposite sides of said central opening.

9. The excitation light source assembly of claim 1, wherein the light source positioned within each of the plurality of lamp receptacles does not extend beyond the lamp receptacle.

10. The excitation light source assembly of claim 1, further comprising a plurality of light sources positioned within at least some of the lamp receptacles so that the plurality of light sources do not extend beyond the lamp receptacles.

11. The excitation light source assembly of claim 10, wherein said plurality of light sources is three light sources.

12. The excitation light source assembly of claim 1, wherein the plurality of light receptacles defined by said housing comprise a plurality of large diameter receptacles and a plurality of small diameter receptacles.

13. The excitation light source assembly of claim 1, wherein the plurality of light receptacles defined by said housing comprise generally cylindrically shaped openings having first and second open ends, said excitation light source assembly further comprising a circuit board mounted to a first side of said housing, said light sources being mounted to said circuit board so that said light sources extend through the first open ends of the generally cylindrically-shaped light receptacles.

14. An assembly, comprising:
a support structure;
a camera mounted to said support structure;
an excitation light source assembly mounted to said support structure, said excitation light source assembly comprising:
a housing defining a central opening therein and a plurality of lamp receptacles surrounding the central opening, said housing being mounted to said support structure so that the central opening is aligned with said camera and so that a field of view of said camera is substantially unobstructed by said housing;
at least one narrow-band light source positioned within at least one of the plurality of lamp receptacles; and
a diffuser positioned within at least some of the plurality of lamp receptacles, each of said diffusers diffusing light produced by each of said narrow-band light sources; and
a control system operatively connected to each of said narrow-band light sources, said control system operating selected ones of said narrow-band light sources to provide a desired excitation illumination to a fluorescent material within the field of view of said camera, the fluorescent material fluorescing in response to the excitation illumination.

15. The assembly of claim 14, further comprising a light filter positioned adjacent each of the diffusers.

16. The assembly of claim 14, wherein each of the lamp receptacles defined by said housing are angled with respect to a central axis of said housing so that light emitted from each of said narrow-band light sources is directed to a desired area within the field of view of said camera.

17. The assembly of claim 14, wherein each of said narrow-band light sources is selected to provide desired number of illumination bands over a desired spectral range.

18. The assembly of claim 17, wherein the desired spectral range is from about 430 nm to about 745 nm.

19. The assembly of claim 17, wherein the desired number of illumination bands is 10.

20. The assembly of claim 17, wherein each desired illumination band has a bandwidth ranging from about 30 nm to about 35 nm.

21. The assembly of claim 17, wherein the desired spectral range is from about 430 nm to about 900 nm.

22. The assembly of claim 17, wherein the desired spectral range is from about 430 nm to about 800 nm.

23. The assembly of claim 14, wherein each of said narrow-band light sources comprises a light emitting diode.

24. The assembly of claim 14, wherein said housing comprises a polyoxymethylene thermoplastic material.

25. An excitation light source assembly, comprising:
a housing defining a central opening therein and a plurality of lamp receptacles therein surrounding the central opening, said housing being mountable to a support structure so that the central opening is aligned with a camera also mounted to the support structure so that a field of view of the camera is unobstructed by said housing;
a light source positioned within each of the plurality of lamp receptacles so that said light sources do not extend beyond the lamp receptacles, wherein at least one of said light sources comprises a narrow-band light source; and
a control system operatively connected to each of said light sources, said control system operating selected ones of said light sources to provide a desired excitation illumination to an object within the field of view of the camera, th excitation illumination causing fluorescent materials in the object to fluoresce, the camera capturing an image of the fluorescing material in the object.

26. The excitation light source assembly of claim 25, wherein said plurality of lamp receptacles defined by said housing comprise a plurality of large diameter lamp receptacles and a plurality of small diameter lamp receptacles, said large diameter lamp receptacles receiving a plurality of said light sources, said small diameter receptacles receiving a single light source.

27. The excitation light source assembly of claim 25, wherein the plurality of light receptacles defined by said housing comprise generally cylindrically shaped openings having first and second open ends, said excitation light source assembly further comprising a circuit board mounted to a first side of said housing, said light sources being mounted to said circuit board so that said light sources extend through the first open ends of the generally cylindrically shaped light receptacles.

\* \* \* \* \*